United States Patent [19]

Novicky

[11] 4,303,772

[45] Dec. 1, 1981

[54] OXYGEN PERMEABLE HARD AND SEMI-HARD CONTACT LENS COMPOSITIONS METHODS AND ARTICLES OF MANUFACTURE

[75] Inventor: Nick N. Novicky, Buffalo Grove, Ill.

[73] Assignee: George F. Tsuetaki, Chicago, Ill.

[21] Appl. No.: 72,449

[22] Filed: Sep. 4, 1979

[51] Int. Cl.³ .................... C08F 220/26; G02C 7/04
[52] U.S. Cl. ................ 526/279; 351/160 R; 351/160 H; 526/264
[58] Field of Search .............. 526/279, 264; 351/160 R, 160 H

[56] References Cited

U.S. PATENT DOCUMENTS 4,056,496 11/1977 Mancini et al. ................ 526/320
4,120,570 10/1978 Gaylord ................ 264/1
4,139,513 2/1979 Tanaka et al. ............ 260/29.6 TA
4,139,692 2/1979 Tanaka et al. .............. 526/218

Primary Examiner—Harry Wong, Jr.
Attorney, Agent, or Firm—James T. FitzGibbon

[57] ABSTRACT

The invention relates to new monomers of a polysiloxanyl alkyl esters of acrylic and methacrylic acids and its copolymerization with alkyl esters of acrylic, methacrylic acids and/or itaconate esters to produce highly permeable contact lens material. The copolymer preferably includes a cross-linking agent and hydrophilic monomer. Contact lenses manufactured from the material are easily machined and polished into hard or semi-hard contact lenses having excellent dimensional stability.

4 Claims, No Drawings

OXYGEN PERMEABLE HARD AND SEMI-HARD CONTACT LENS COMPOSITIONS METHODS AND ARTICLES OF MANUFACTURE

BACKGROUND OF THE INVENTION

The present invention relates to novel chemical compounds, polymers made from such compounds and novel materials and products made from such compounds. In particular, one important use of the materials made from the invention is the manufacture of corneal contact lenses.

In recent years, corneal contact lenses have become more and more popular in the United States and throughout the world.

The great popularity of contact lenses is easily understood. One important reason is that such lenses provide perhaps the best possible manner of achieving optical correction for the eyes. The lenses fit directly over the eye, and when properly fitted, are easily retained in place. Problems common with spectacles, such as interference with peripheral vision, moving about on the head, discomfort, and the possibility of improper interpupilary distance, are easily overcome. Contact lenses provide cosmetic advantages and afford convenience and increased safety when used in diverse pursuits, particularly sporting events.

Contact lenses, which were originally made from glass, were gradually improved as improved materials became available. Now most commonly used contact lenses are generally subdivided into two types, so-called hard contact lenses, and soft contact lenses. Each type of lens has its own advantages, but each also includes certain disadvantages.

Referring first to the advantages of hard contact lenses, these lenses provide dimensional stability, so that the characteristics of an optical prescription will remain unchanged while the lens is in use in the eye. In some cases, the eye will actually conform to the contour of the lens over a period of time so as to improve the vision of the wearer. Moreover, hard contact lenses are relatively durable in relation to soft lenses.

While hard contact lenses have the above and other advantages, some patients find such lenses somewhat uncomfortable in use, and prefer the so-called soft contact lens. These lenses fall generally into three categories, namely lenses made from silicone rubber or like materials, lenses made from "HEMA" (hydroxyethylmethacrylate) or so-called "hydrogel" lenses, and finally, lenses of the methyl methacrylate base type, modified by the addition of polymers such as cellulose acetate butyrate ("CAB"). Soft lenses readily conform to the eye and are quite comfortable in short term use. They are extremely thin as well as soft and pliable. However, they do not provide satisfactory oxygen transmissibility through the lens.

Referring now to the disadvantage of both soft and hard contact lenses, neither type of lens is able to be worn by a user over an extended period of time because both types of lenses are not enough permeable to the oxygen. As a result, the cornea is unable to "breathe" properly. Consequently, after a period of time, the cornea becomes irritated or perhaps even damaged. Moreover, the lenses sometime tend to adhere to the eye of the wearer after being in place for an unduly long period of time, and this can cause discomfort and even damage to the eye.

In view of the foregoing advantages of contact lenses, it would be even further advantageous if there were a contact lens that possessed the known advantages of machinability, dimensional stability, toughness and optical clarity, and which were also sufficiently oxygen permeable to be worn by a user for an extended period, such as for several days, weeks, or even months or more. Users of such lenses, could wear them for extended periods and still feel comfortable, could have good vision and not risk injuring their eyes. Contact lenses which could be worn for an extended period would eliminate common problems with existing lenses. These problems include losing or misplacing the lenses because of frequent handling, wear and tear occasioned by such handling, and the general inconvenience of locating and inserting the lenses when they are needed, but not being worn.

Still further, the anticipated life of an extended duration contact lens would be lengthened considerably. This is because the requirement for handling would be very greatly reduced. At present, the frequent handling of relatively dilicate lenses, and the requirement that they be cleaned frequently, is largely responsible for the premature degeneration of many such lenses. For example, it is not uncommon for a pair of hydrogel lenses costing perhaps hundreds of dollars, to last for only about one year or so without cracking or becoming torn as a result of frequent handling. More sturdy lenses, such as known types of hard lenses, are not susceptible to tearing or cracking, but can be scratched by frequent removal and insertion, and cleaning, particularly if they are dropped occasionally. Losing the lenses is a realistic possibility which could be minimized substantially by having lenses which are removed weekly, or monthly, or at greater intervals.

Referring now to prior attempts to provide polymers with increased oxygen permeability, normally, most or all such known polymers have either been too dimensionally unstable for satisfactory use, or have had other disadvantages. For example, it is known to add significant amounts of additives normally intended to increase wettability. While such materials are helpful in proper amounts, using excess amounts thereof has often tended to cause proteinaceous matter to deposit on and impair the transparency of the inner surface of the lens.

While numerous attempts have been made to improve the oxygen permeability of both hard and soft contact lenses, the attempts have met with only limited success, particularly in thicker lenses. Moreover, many soft lens material provide an environment which is highly suitable for bacterial growth, and this calls for sterilization procedures which in turn require the lenses to be handled frequently.

The present invention, therefore, is intended from the standpoint of an end use product to provide contact lens materials which are sufficiently oxygen permeable that they may be worn by the user on a greatly extended basis in relation to prior art lenses, which do not have the disadvantages associated with known prior art lenses intended for this purpose.

Referring now to its chemical aspects, the invention relates to the manufacture of copolymers of an acrylic or methacrylic material of a known type and novel, silicone substitute acrylic or methacrylic compounds so as to produce an oxygen permeable plastic material which is uniquely suitable for manufacturing novel corneal contact lenses as referred to above. The expression "copolymers" is sometimes used herein for simplicity in referring to a polymer which includes two principal comonomers, although such polymer may incidentally include one or more additional known monomers in minor amounts for purposes such as cross-linking, increasing the wettability of the final product, or otherwise.

The copolymer compositions and products made therefrom, are improved over counterpart prior art compositions by reason of increased dimensional stability and improved gas permeability. Such novel compositions also retain or provide improvements in desirable prior art characteristics such as optical clarity, the ability to be cast, molded and machined, and compatability with chemically bonded, hydrophilic materials adapted to improve the wettability of the finished product.

Preferably, the compositions comprise high molecular weight polysiloxanylalkylesters of acrylic and methacrylic acids and other compositions as monomers, copolymerized with methacrylates or other esters of acrylic or methacrylic acids, vinyl carbazole, vinyl benzenes or vinyl pyrrolidinone.

According to the invention, one comonomer (the "first" comonomer) is an acrylic or methacrylic ester silane, substituted with one or more highly substituted siloxanyl groups. Two such typical comonomers are nonamethyltetrasiloxanyl- or decamethylpentasiloxanylmethacryloxyalkylsilane, which can be copolymerized with an alkyl acrylate or alkyl methacrylate, (the "second" comonomer), with this copolymer composition in turn being cross-linked to a slight degree by cross-linking agents, and preferably further modified by the addition of compounds intended to increase the wettability of the finished copolymer material. This basic polymerization of the novel comonomers with known comonomers occurs through a known double-bond polymerization mechanism.

A certain proportion, such as 10% to 60% of this compound, is then polymerized with one or more or other second comonomer compounds having the same or similar acrylic or methacrylic ester portion, together with the minor amounts of cross-linking and wetting agents, referred to above.

One more aspect of the present invention relates to the method of making the so-called first or novel comonomers of the invention. According to this method, chlorosilanes are reacted with hydroxy derivatives of polysiloxanyl groups, in the presence of pyridine to bond released hydrochloric acid in the form of precipitated salt of pyridinium hydrochloride at low temperatures. The details of this method are brought out in other portions of the specification. In still another aspect, the invention relates to alternate methods of preparing the above or similar products. One alternate method comprises reacting others, mono-, di- or methacryloxypropyltrichlorosilanes with an excess of pyridine and reacting the resulting intermediates with polysilanols (tetra or penta) at −50° C.

Monomer is removed from these reaction mixtures by purification following removal of the low molecular weight materials, with the reaction products being purified by washing with weak alkalies or like materials.

The novel comonomer compounds of the present invention can be represented by the following formulas:

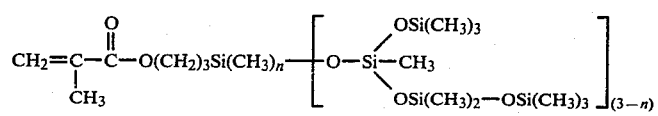

where n is an integer 0, 1, 2.
and by:

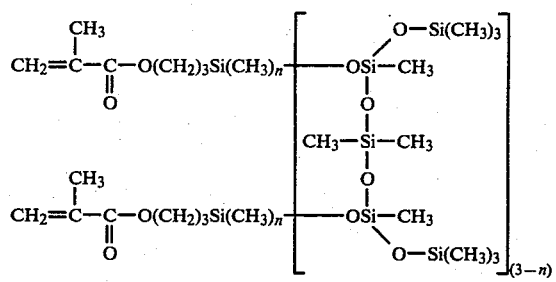

where n is an integer of 0, 1, 2.

In the alkyl or phenyl ester second principal comonomer, the alkyl group contains 1 to about 10 carbon atoms, (typically one to six carbon atoms) and the phenyl ester contains a single phenyl group, N-vinyl carbazole, N-vinyl pyrrolidinone, ethyl vinyl benzene and divinyl benzenes.

One compound which may be used as the first principal comonomer of the present invention is a nonamethyltetrasiloxanylmethacryloxypropyldimethylsilane:

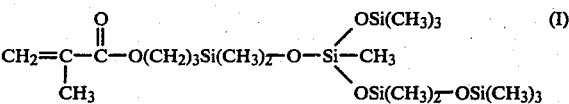

another compound is bis(nonamethyltetrasiloxanyl)methacryloxypropylmethylsilane:

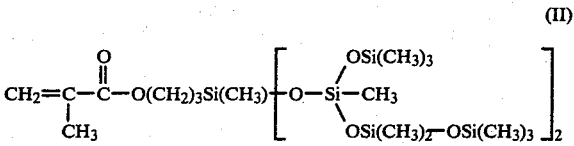

still another compound is tris(nonamethyltetrasiloxanyl)methacryloxypropylsilane:

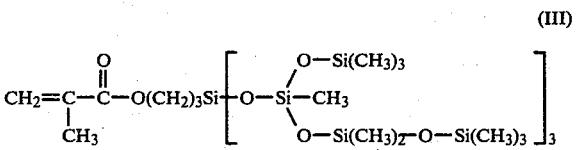

another suitable compound is decamethylpentasiloxanyl-di(methacryloxypropyldimethylsilane):

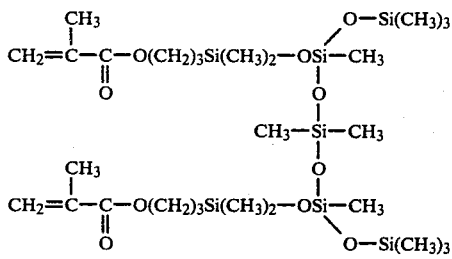

One more suitable compound is bis(decamethylpentasiloxanyl)di(methacryloxypropylmethylsilane):

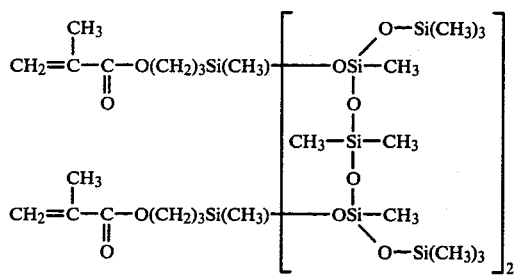

The last suitable compound is tris(decamethylpentasiloxanyl)di(methacryloxypropylsilane):

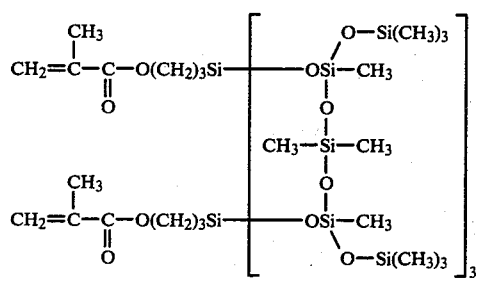

Representative known or second comonomers which may be employed in the practice of the invention include the following:
 methyl acrylate, methyl methacrylate
 ethyl acrylate, ethyl methacrylate
 propyl acrylate, propyl methacrylate
 isopropyl acrylate, isopropyl methacrylate
 2-ethylhexyl acrylate, 2-ethylhexyl methacrylate
 cyclohexyl acrylate, cyclohexyl methacrylate
 benzyl acrylate, benzyl methacrylate
 phenyl acrylate, phenyl methacrylate
 N-vinyl carbazole, N-vinyl pyrrolidinone
 3-hydroxy 2-naphthyl methacrylate
 ethyl vinyl benzene, divinyl benzenes
 dimethyl itaconate, dibutyl itaconate Such secondary comonomers are preferably present in an amount of from about 40$ to 90% of the composition.

Cross-linking monomers include difunctional compounds such as:
 ethyleneglycoldimethacrylate
 diethyleneglycoldimethacrylate
 triethyleneglycoldimethacrylate
 tetraethyleneglycoldimethacrylate
 polyethyleneglycoldimethacrylate
 divinyl benzene
 tetramethyldisiloxane di(methylmethacrylate) and mixtures thereof. From 0% to about 10% by weight of such cross-linking monomers may be used.

The wetting agents include, but are not limited to:
 acrylic acid
 methacrylic acid
 N-vinyl 2-pyrrolidone, and
 hydroxyalkyl esters of acrylic and methacrylic acids, and mixtures thereof. From 0% to 20% by weight of such wetting agents may be used in the composition.

In view of the shortcomings of prior art contact lenses and the compounds and compositions used in making them, it is an object of the present invention to provide novel monomers useful in making improved lens materials, improved polymer compositions made from such novel monomers, and improved lenses made from such polymers.

Another object of the invention is to provide novel silicone compounds used as components of polymerizable monomers.

A still further object is to provide a method of making starting or intermediate materials for making novel silicone compounds, and to provide starting and intermediate materials for other uses as well.

Yet another object is to provide highly branched or substituted silane, silanol and siloxane materials for a variety of uses, including the manufacture of copolymers, terpolymers or other polymer incorporating such materials.

A still further object is to provide one or more compounds containing alkyl esters of acrylic or methacrylic acids, and incorporating one, two, or three polysiloxanylalkyl groups.

A still further object is to provide an optically useful, novel polymeric material of increased oxygen permeability with respect to prior art compounds.

Still another object is to provide a material of the foregoing type which may be formulated or synthesized so as to have a desirably high refractive index, and which can therefore be used in the manufacture of bifocal contact lenses, particularly fused bifocal contact lenses.

A still further object is to provide a composition which will make possible the manufacture of corneal contact lenses which can be worn for an extended time period while providing greatly increased comfort to the wearer.

Another object is to provide a polymeric contact lens material which is compatible with additives of known kinds used to provide other desirable end use properties.

A further object is to provide an oxygen-permeable polymer which has non-optical uses, such as forming membranes or containers for blood or other dialyzable material which can be purified by absorption of oxygen and/or transpiration or loss of other gaseous components, and for making apparatus for transferring blood or other material to and from, and through dialysis machines, for example.

A still further object is to provide a method of manufacturing copolymers incorporating the compositions made by the novel methods referred to above.

These and other objects and advantages of the invention, including those inherent therein, may be achieved in practice by carrying out the methods, and making the compounds and compositions referred to herein. The following examples, which are set forth by way of illustration and not by way of limitation, illustrate preferred methods of carrying the invention into practice.

DESCRIPTION OF THE PREFERRED EMBODIMENTS OF THE INVENTION

EXAMPLE 1

This example illustrates a preparation of nonamethylchlorotetrasiloxane which is useful as an intermediate in preparing other compounds.

1.0 mole of nonamethyltetrasiloxane and 1.1 moles of dry pyridine is diluted with 1700 ml of dry n-hexane in a 3 liter, 3 necked, round bottom flask. The flask is equipped with a mechanical stirrer and thermometer, and is cooled to less than 8° C. by an ice bath.

Chlorine gas is then introduced through the gas inlet tube. A white precipitate of pyridinium hydrochloride in formed. The temperature is maintained in the range of 5°–8° C., while chlorine is bubbled through the reaction mixture. Cessation of the exotherm indicates that the reaction is complete. Pyridinium hydrochloride is isolated by filtration and then discarded. Then n-hexane and the excess of pyridine is removed by means of distillation and the product is analyzed by IR spectroscopy. The complete disappearance of Si-H band at about 2200 cm$^{-1}$ region concludes that the reaction is completed.

EXAMPLE 2

This example illustrates a preparation of a new and useful monomer, Tris(nonamethyltetrasiloxanyl)methacryloxypropylsilane.

Step 1

Nonamethylchlorotetrasiloxane (300 g.) is dissolved in 1200 ml of diethylether and placed in a 3 liter, 3 necked, round bottom flask equipped with a mechanical stirrer, a thermometer and additional funnel, and cooled to 0° C. in the ice bath. After flushing the system with nitrogen for 15 minutes, when the temperature reaches 0° C., start titration with saturated aqueous solution of sodium bicarbonate. The pH of the reaction mixture is controlled so as to remain neutral. After all the sodium bicarbonate solution is added, the pH still remains above 6.9–7.0, the organic layer is separated and dried over anhydrous magnesium sulfate for 30 minutes. Magnesium sulfate is filtered by means of a frit filter type C. Crude nonamethyltetrasiloxanol is holding for Step 2, Example 2.

Step 2

Trichloromethacryloxypropylsilane (82 g.) is dissolved in 700 ml of dry diethylether and placed in a 3 liter, 3 necked, round bottom flask equipped with a mechanical stirrer, a thermometer and an additional funnel. The solution is cooled down to −50° C. with a dry ice-isopropanol cooling bath. When the temperature has reached −50° C., 85 grams (slight excess) of dry pyridine is added over a period of about 2 hours, with the temperature being held at −50° C. or less during pyridine addition. At the same temperature, an equimolar amount of nonamethyltetrasiloxanol, which can be that prepared as disclosed above, is added in a diethylether solvent, forming a white precipitate of pyridinium hydrochloride. When all the nonamethyltetrasiloxanol has been added, the temperature of the reaction mixture is increased rapidly to about +30° C. and stirred for ½ hour. The pyridinium hydrochloride is isolated by filtration and the filter cake is washed with diethylether.

The crude monomer tris(nonamethyltetrasiloxanyl)methacryloxypropylsilane in diethylether is washed twice with water (200 ml's each). The upper (organic) layer is then separated and diethylether is removed by means of distillation. The crude monomer (III) is washed with 150 ml of distilled water, and thereafter twice with a dilute sodium bicarbonate solution, again with distilled water once, and then dried over anhydrous magnesium sulfate for 2 hours. The dried monomer is purified by distilling off all low boiling materials at 85° C. and 0.1 mm Hg pressure. The purified monomer is refrigerated until used. Density of the monomer (III) is 0.98 g/ml at 20° C. and $n_D^{25} = 1.4185$.

EXAMPLE 3

This example illustrates a preparation of a new and useful monomer, bis(Decamethylpentasiloxanyl)di(methacryloxypropylmethylsilane).

Step 1

Decamethyldichloropentasiloxane (375 g.) is dissolved in 1400 ml of n-hexane and placed in a 3 liter, 3 necked, round bottom flask equipped with a mechanical stirrer, a thermometer and additional funnel, and cooled to 0° C. in the ice bath. After flushing the system with nitrogen for 15 minutes, when the temperature reaches 0° C., start titration with saturated aqueous solution of sodium bicarbonate, The pH of the reaction mixture is controlled so as to remain neutral. After all the sodium bicarbonate solution is added, the pH still remains about 6.9–7.0, the organic layer is separated and dried over anhydrous magnesium sulfate for 30 minutes. Magnesium sulfate is filtered by means of a frit filter type C. Crude decamethyldihydroxypentasiloxane is holding for Step 2, Example 3.

Step 2

Dichloromethacryloxypropylmethylsilane (204 g.) is dissolved in 1000 ml of dry n-hexane and placed in a 3 liter, 3 necked, round bottom flask equipped with a mechanical stirrer, a thermometer and an additional funnel. The solution is cooled down to −50° C. with a dry ice-isopropanol cooling bath. When the temperature has reached −50° C., 170 grams (slight excess) of dry pyridine is added over a period of about 2 hours, with the temperature being held at −50° C. or less during pyridine addition. At the same temperature, 330 grams of decamethyldihydroxypentasiloxane, which can be that prepared in Step 1 of Example 3, is added in a n-hexane solution, forming a white precipitate of pyridinium hydrochloride. When all the decamethyldihydroxypentasiloxane has been added, the temperature of the reaction mixture is increased rapidly to about +30° C. and stirred for ½ hour. The pyridinium hydrochoride is isolated by filtration and the filter cake is washed with n-hexane.

The crude monomer bis(Decamethylpentasiloxanyl)-di(methacryloxypropylmethylsilane) in n-hexane is washed twice with water (200 ml's each). The upper (organic) layer is then separated and n-hexane is removed by means of distillation. The crude monomer (V) is washed with 150 ml of distilled water, and thereafter twice with a dilute sodium bicarbonate solution, again with distilled water once, and then dried over anhydrous magnesium sulfate for 2 hours. The dried monomer is purified by distilling off all low boiling materials at 85° C. and 0.1 mm Hg pressure. The purified monomer is refrigerated until used. Density of the monomer (V) is 0.995 g/ml at 20° C.

EXAMPLE 4

This example illustrates the preparation of a representative oxygen permeable copolymer.

A mixture of 35 parts of the comonomer (III) of Example 2, 60 parts of methyl methacrylate, 3 parts of methacrylic acid and 2 parts of diethyleneglycoldimethacrylate and 0.14% by weight of the entire mixture of tert-butyl peroxypivalate is placed in a glass dish or tube and then placed in a vacuum oven which has been purged with nitrogen. The oven is closed and the temperature is maintained at 48° C. for 24 hours. The monomers react to create a copolymer plastic which is hard, colorless, transparent and rigid. The oxygen permeability should be about $19.6 \times 10^{-11}$ (cm$^2$/sec)(ml O$_2$/ml$\times$mm Hg). The oxygen permeability of a disc of polymethylmethacrylate, measured in the same way is less $0.2 \times 10^{-11}$ (cm$^2$/sec)(ml O$_2$/ml$\times$mm Hg), while that of a disc of hydrated polyhydroxyethylmethacrylate is $8 \times 10^{-11}$ (same units).

EXAMPLE 5

This example illustrates the preparation of a representative oxygen permeable copolymer from another comonomer (V).

A mixture of 45 parts of novel comonomer (V) of Example 3, 60 parts of methyl methacrylate, 10 parts of cyclohexyl methacrylate, 2 parts of N-vinyl pyrrolidone and 3 parts of triethyleneglycoldimethacrylate and 0.25% by weight of the entire composition of t-butyl peroxydecanoate is polymerized in a polypropylene dish or tube at 50° C. for 24 hours. The resulting copolymer plastic material is machined, cut, polished, and finished into a concavoconvex lens of 0.20 mm thickness. The oxygen permeability of this lens should be about $18.6 \times 10^{-11}$ (cm$^2$/sec)(ml O$_2$/ml$\times$mm Hg). (155 mm Hg is the normal partial pressure of oxygen in a 760 mm Hg atmosphere). This particular type of measurement can be made by a "Schema-Versatae" Model 920 gas flux meter which is known and widely used in the contact lens industry.

The following Examples 6–18 illustrate the conditions of preparation and properties of copolymers which contain varying proportions of the novel comonomer of Example 2 when such comonomers are reacted with one or more of the following compounds:

methyl methacrylate (MMA)
cyclohexyl methacrylate (CHMA)
methacrylic acid (MAA)
N-vinyl pyrrolidone (NVP)
triethyleneglycoldimethacrylate (Tri-EGDMA)
tetraethyleneglycoldimethacrylate (TEGMA)
ethyleneglycoldimethacrylate (EGDMA)

The siloxane comonomer used in these examples is that prepared in Example 2, namely, tris(nonamethyltetrasiloxanyl)methacryloxypropylsilane (III), and which is abbreviated in the table below as C(III).

The polymerization is conducted in polypropylene tubes for 24 hours at the temperature shown in the table. The table also shows the composition of each form of polymer, and the temperature at which polymerization took place. The properties of the polymer are abbreviated in the right hand corner, with the meanings of the abbreviations appearing below.

In the examples, the principal polymers are C(III) and MMA, with the compositions including one or more other compounds as indicated. MAA provides wettability, CHMA supplements the MMA to accomplish better rigidity, and NVP provides increased wettability, except that, where more than 4 or 5% NVP is present, a portion thereof serves as a third monomer. The TEGDMA, Tri-EGDMA, EGDMA and DVB (divinylbenzene) are cross-linking agents.

| | | | COMPOSITION, WT., PERCENT | | | | | | | | |
|---|---|---|---|---|---|---|---|---|---|---|---|
| Example | C(III) | MMA | CHMA | MAA | NVP | Tri-EGDMA | TEGDMA | EGDMA | DVB | TEMP °C. | PROP. |
| 6 | 35 | 57 | | 3 | | | | 2 | 3 | 49 | T,H,R |
| 7 | 40 | 50 | 10 | | | | | | | 50 | T,H,R |
| 8 | 45 | 35 | 10 | 4 | 2 | 4 | | | | 45 | T,H,R |
| 9 | 60 | | 40 | | | | | | | 45 | T,H,R |
| 10 | 38 | 45 | 10 | 3.5 | | 3.5 | | | | 47 | T,H,R |
| 11 | 36 | 25 | 30 | 4.5 | | 4.5 | | | | 43 | T,H,R |
| 12 | 34 | 40 | 26 | 4 | 4 | | | 3 | | 46 | T,H,R |
| 13 | 37 | 27 | 27 | | 5 | | 4 | | | 49 | T,H,R |
| 14 | 25 | 75 | | | | | | | | 40 | T,H,R |
| 15 | 50 | | 50 | | | | | | | 45 | T,H,R |
| 16 | 42 | 27 | 27 | 2 | | | | 2 | | 43 | T,H,R |
| 17 | 40 | 42 | 10 | 4.5 | | 3.5 | | | | 45 | T,H,R |
| 18 | 38 | 45 | 8 | 4.7 | | 3.6 | | | 0.7 | 46 | T,H,R |

T = Transparent
H = Hard
R = Rigid

Products of the invention herein described as "hard" have a hardness, measured on the Shore D scale of about 82–90, (ASTM 2240) while polymethylmethacrylate, tested the same way, has a hardness of 90–93.

EXAMPLE 19

This example illustrates the preparation and properties of a wettable, oxygen permeable polymer. A disc is prepared in the manner described in Example 5 from a mixture of 40 parts of the bis(decamethylpentasiloxanyl)di(methacryloxypropylmethylsilane) (V) of Example 3, 40 parts of methyl methacrylate, 5 parts of N-vinyl pyrrolidone and 15 parts of dimethyl itaconate, using t-butylperoxypivalate as a catalyst. The polymerization is carried out at 48° C. for 24 hours. The resulting disc is colorless, transparent, hard and rigid. The oxygen permeability of the polymer should be about $23.2 \times 10^{-11}$ (cm$^2$/sec)(ml O$_2$/ml mm Hg). In this example, no difunctional cross-linking agent was used.

EXAMPLE 20

This example illustrates the preparation of a copolymer of methyl methacrylate and the novel comonomer (III) referred to in Example 2.

A cylindrical plug of the copolymer is prepared by polymerizing a mixture of 40 parts of such novel comonomer (III), 50 parts of methyl methacrylate, 5 parts of vinyl carbazole and 5 parts of divinyl benzene, in the presence of t-butylperoxydecanoate at 45° C. Lenses prepared from the plug are hard, rigid, transparent, and highly oxygen permeable in relation to prior art lenses.

EXAMPLE 21

This example illustrates the preparation of a copolymer of methyl methacrylate and the novel comonomer (II), bis(nonamethyltetrasiloxanyl)methacryloxypropylmethylsilane. (The novel comonomer (II) is prepared by the chemistry described in Example 2 or Example 3.)

A mixture of 37 parts of the comonomer (II), 58 parts of methyl methacrylate, 3 parts of methacrylic acid and 2 parts of triethyleneglycoldimethacrylate and 0.135% by weight of the entire mixture of t-butyl peroxypivalate is polymerized in polypropylene tube at 48° C. for 24 hours; then insert to 108° C. thermostated oven for an additional 24 hours to finalize polymerization. Lenses prepared from this polymer plastic are hard, rigid, transparent, and highly oxygen permeable.

EXAMPLE 22

This example illustrates the preparation and properties of a wettable, oxygen permeable copolymer. A disc is prepared in the manner described in Example 21 from a mixture of 36 parts of comonomer (IV), decamethylpentasiloxanyl-di(methacryloxypropyldimethylsilane). (The novel comonomer (IV) is prepared by the chemistry described in Example 2 or Example 3.) 40 parts of methyl methacrylate, 4 parts of methacrylic acid, 16 parts of dimethyl itaconate and 4 parts of triethyleneglycoldimethacrylate, using t-butylperoxypivalate as a catalyst. The polymerization is carried out at 47° C. for 24 hours. The resulting disc is colorless, transparent, hard and rigid.

The previous Examples illustrate the outstanding properties of the resulting polymers of this invention. The polymers referred to may be made from the materials described specifically in detail in the Examples, or may be made as therein illustrated from the other monomers described herein. The desirable properties of the finally produced copolymers result from the use of one or more of the novel silicone comonomers referred to herein.

Other additives to the polymers of this invention, as known in the art, can be made. In all cases, the polymers are optically clear and transparent and meet required standards of desirably high oxygen permeability in semi-rigid and hard contact lenses.

Even though I have described specific examples of this invention, there are many variations possible within the scope of keeping the physical properties as previously described. Such variations include the use of mixtures of monomers within the components to comprise of the required parts of each. For example, two or more siloxanyl alkyl ester comonomers can be used instead of a single such comonomer for the component of the composition. Respectively, two or more cross-linking agents can be used. Other additives to the copolymers such as colorants, tints and like materials may also be employed within the scope of normal ranges of this invention.

What is claimed is:

1. An oxygen permeable, hard or semi-hard, machinable, dimensionally stable, wettable, contact lens material of high transparency consisting essentially of a polymer formed by free radical polymerization of
   (a) 10% to 60% by weight of at least one silicon-containing monomer selected from the class consisting of nonamethyltetrasiloxanylmethacryloxypropyldimethylsilane having the following formula:

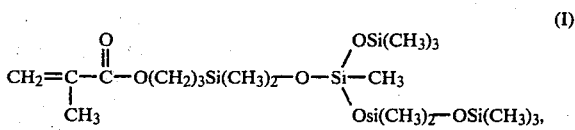

bis(nonamethyltetrasiloxanyl)methacryloxypropylmethylsilane having the following formula:

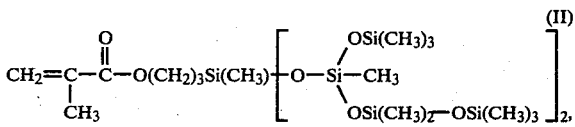

tris(nonamethyltetrasiloxanyl)methacryloxypropylsilane having the following formula:

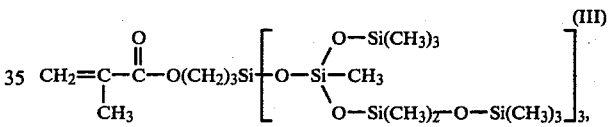

decamethylpentasiloxanyl-di(methacryloxypropyldimethylsilane) having the following formula:

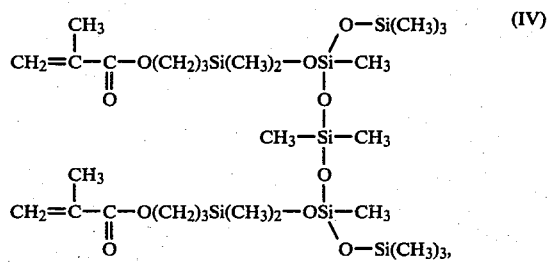

bis(decamethylpentasiloxanyl)di(methacryloxypropylmethylsilane) having the following formula:

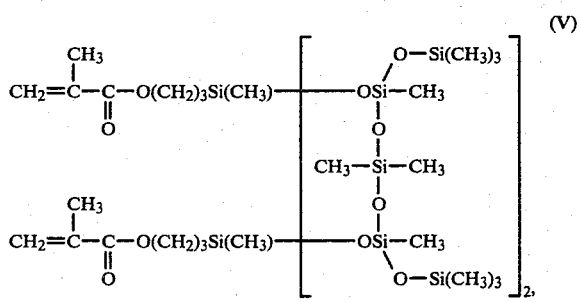

tris(decamethylpentasiloxanyl)di(methacryloxy-propylsilane) having the following formula:

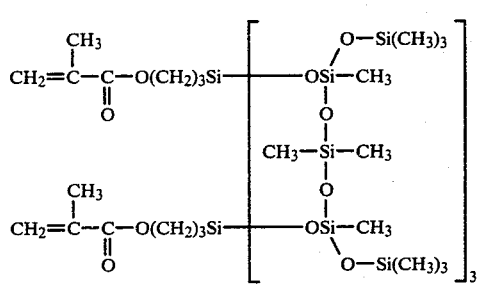
(VI)

and mixtures thereof, (b) 40% to 90% by weight of at least one secondary comonomer selected from the group consisting of methyl acrylate, methyl methacrylate, ethyl acrylate, ethyl methacrylate, propyl acrylate, propyl methacrylate, isopropyl acrylate, isopropyl methacrylate, 2-ethylhexyl acrylate, 2-ethylhexyl methacrylate, cyclohexyl acrylate, cyclohexyl methacrylate, benzyl acrylate, benzyl methacrylate, phenyl acrylate, phenyl methacrylate, N-vinyl pyrrolidinone, 3-hydroxy 2-naphthyl methacrylate, ethyl vinyl benzene, divinyl benzene, methyl itaconate, butyl itaconate, dimethyl itaconate, dibutyl itaconate and mixtures thereof, (c) 0% to 20% by weight of a monomer adapted to act as a wetting agent, and (d) from about 0% to 10% by weight of at least one cross-linking monomer, said weight percents of (a), (b), (c) and (d) being based on the total weight of the entire composition.

2. An oxygen permeable contact lens material as set forth in claim 1 wherein said silicon-containing monomer is tris(nonamethyltetrasiloxanyl)methacryloxypropylsilane.

3. An oxygen permeable contact lens material as set forth in claim 1 wherein said silicon-containing monomer is bis(decamethylpentasiloxanyl)di(methacryloxypropylmethylsilane).

4. An oxygen permeable, hard or semi-hard, machinable, dimensionally stable, wettable, contact lens material of high transparency consisting essentially of a polymer formed by free radical polymerization of (a) 10% to 60% by weight of at least one silicon-containing monomer selected from the class consisting of decamethylpentasiloxanyl-di(methacryloxypropyldimethylsilane) having the following formula:

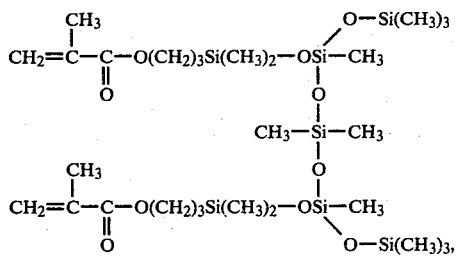

bis(decamethylpentasiloxanyl)di(methacryloxypropylmethylsilane) having the following formula:

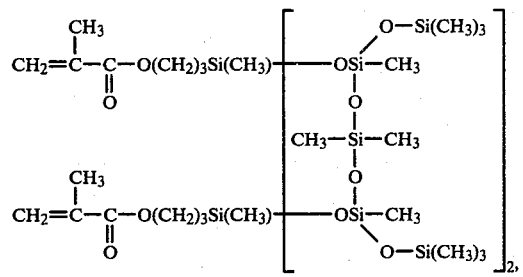

tris(decamethylpentasiloxanyl)di(methacryloxypropylsilane) having the following formula:

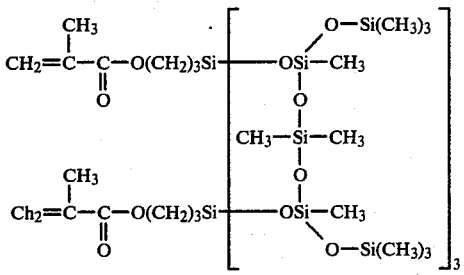

and mixtures thereof, (b) 40% to 90% by weight of at least one secondary comonomer selected from the group consisting of methyl acrylate, methyl methacrylate, ethyl acrylate, ethyl methacrylate, propyl acrylate, propyl methacrylate, isopropyl acrylate, isopropyl methacrylate, 2-ethylhexyl acrylate, 2-ethylhexyl methacrylate, cyclohexyl acrylate, cyclohexyl methacrylate, benzyl acrylate, benzyl methacrylate, phenyl acrylate, phenyl methacrylate, N-vinyl pyrrolidinone, 3-hydroxy 2-naphtyl methacrylate, ethyl vinyl benzene, divinyl benzene, dimethyl itaconate, dibutyl itaconate and mixtures thereof, (c) 0% to 20% by weight of a monomer adapted to act as a wetting agent, and (d) from about 0% to 10% by weight of at least one cross-linking monomer, said weight percents of (a), (b), (c) and (d) being based on the total weight of the entire composition.

* * * * *

UNITED STATES PATENT AND TRADEMARK OFFICE
CERTIFICATE OF CORRECTION

PATENT NO. : 4,303,772
DATED : December 1, 1981
INVENTOR(S) : Nick N. Novicky

It is certified that error appears in the above—identified patent and that said Letters Patent is hereby corrected as shown below:

Column 2, line 22, delete "dilicate", and in place thereof, insert -- delicate --;

Column 5, line 60, delete "40$", and in place thereof, insert -- 40% --;

Column 10, line 6, delete "TEGMA", and in place thereof, insert -- TEGDMA --;

Column 13, line 36, delete "actas", and in place thereof, insert -- act as --.

Signed and Sealed this

Eleventh Day of May 1982

[SEAL]

Attest:

GERALD J. MOSSINGHOFF

Attesting Officer    Commissioner of Patents and Trademarks